(12) United States Patent
Ishak

(10) Patent No.: US 8,500,274 B2
(45) Date of Patent: *Aug. 6, 2013

(54) DUAL-FILTER OPHTHALMIC LENS TO REDUCE RISK OF MACULAR DEGENERATION

(75) Inventor: Andrew Ishak, Waterford, VT (US)

(73) Assignee: High Performance Optics, Inc., Roanoke, VA (US)

( * ) Notice: Subject to any disclaimer, the term of this patent is extended or adjusted under 35 U.S.C. 154(b) by 627 days.

This patent is subject to a terminal disclaimer.

(21) Appl. No.: 12/080,806

(22) Filed: Apr. 4, 2008

(65) Prior Publication Data

US 2008/0291394 A1 Nov. 27, 2008

Related U.S. Application Data

(63) Continuation-in-part of application No. 11/303,433, filed on Dec. 16, 2005, now Pat. No. 8,403,478, which is a continuation-in-part of application No. 10/856,688, filed on May 28, 2004, now Pat. No. 7,066,596, which is a continuation-in-part of application No. 10/000, 062, filed on Nov. 2, 2001, now abandoned.

(60) Provisional application No. 60/245,304, filed on Nov. 3, 2000.

(51) Int. Cl.
G02C 7/10 (2006.01)
G02C 7/04 (2006.01)

(52) U.S. Cl.
USPC .............. 351/159.6; 351/159.29; 351/159.32; 351/159.65; 351/159.66; 623/6.11; 623/6.6

(58) Field of Classification Search
USPC .......... 351/44, 45, 49, 162, 163, 177, 159.29, 351/159.32, 159.6, 159.65, 159.66; 623/6.11, 623/6.6
See application file for complete search history.

(56) References Cited

U.S. PATENT DOCUMENTS

| | | | | | |
|---|---|---|---|---|---|
| 4,878,748 | A | * | 11/1989 | Johansen et al. | 351/44 |
| 5,528,322 | A | * | 6/1996 | Jinkerson | 351/163 |
| 6,984,038 | B2 | * | 1/2006 | Ishak | 351/163 |
| 7,066,596 | B2 | * | 6/2006 | Ishak | 351/163 |
| 2002/0159026 | A1 | * | 10/2002 | Bernheim | 351/163 |

* cited by examiner

Primary Examiner — Scott J Sugarman
(74) Attorney, Agent, or Firm — Ober, Kaler, Grimes & Shriver; Royal W. Craig

(57) ABSTRACT

An improved dual-filter lens for protective eyewear that combines a first filter for blocking essentially 100% of UV light, and second filter for filtering blue light. The first filter may comprise a multi-layered dielectric mirror layer 14 or Rugate filter 50, and the second filter may comprise dye-impregnated lens layer(s) 16, 18 or Rugate filter 50. The first filter blocks essentially 100% of UV light, while the second filter establishes an increasing transmission profile that cuts on sharply at approximately 415 nm, and establishes an increasing transmission profile between approximately 415 nm to about 475 nm. The cut-on slope rises approximately 0.15% in transmissivity for every nanometer of increasing wavelength change, with a maximum filtering effect within the 440-465 nm range. These dual filters provide a balanced light transmission profile that reduces harmful light transmission and prevents macular degeneration, cataracts and other ocular injuries, while still preserving visual acuity.

16 Claims, 8 Drawing Sheets

For Test: Definition - ANSI Z87.1

| Lens Samples | Lens Sample Group Description | | |
|---|---|---|---|
| one Lens sample Group | Substrate (Lens Material) | | Coatings (Hard Coat, AR, etc) |
| Manufacturer: Bayz | Lens Material: | unk | Type: Polarized |
| Lens Type: FSV | Index of Refraction: | | Comments: |
| Requested By: DR. Ishak | Lens Density: | | Polarized / Amber |
| | Report valid thru: | 09/16/01 | |

| Test Number | Definition | Pass/Fail |
|---|---|---|
| Z-BZS031601-01-01-01 | 20 | Pass |
| Z-BZS031601-01-01-02 | 34 | Pass |
| Z-BZS031601-01-01-03 | 34 | Pass |

ANSI Z87.1 Requirement
Pattern 20 in both directions

FIG. 3

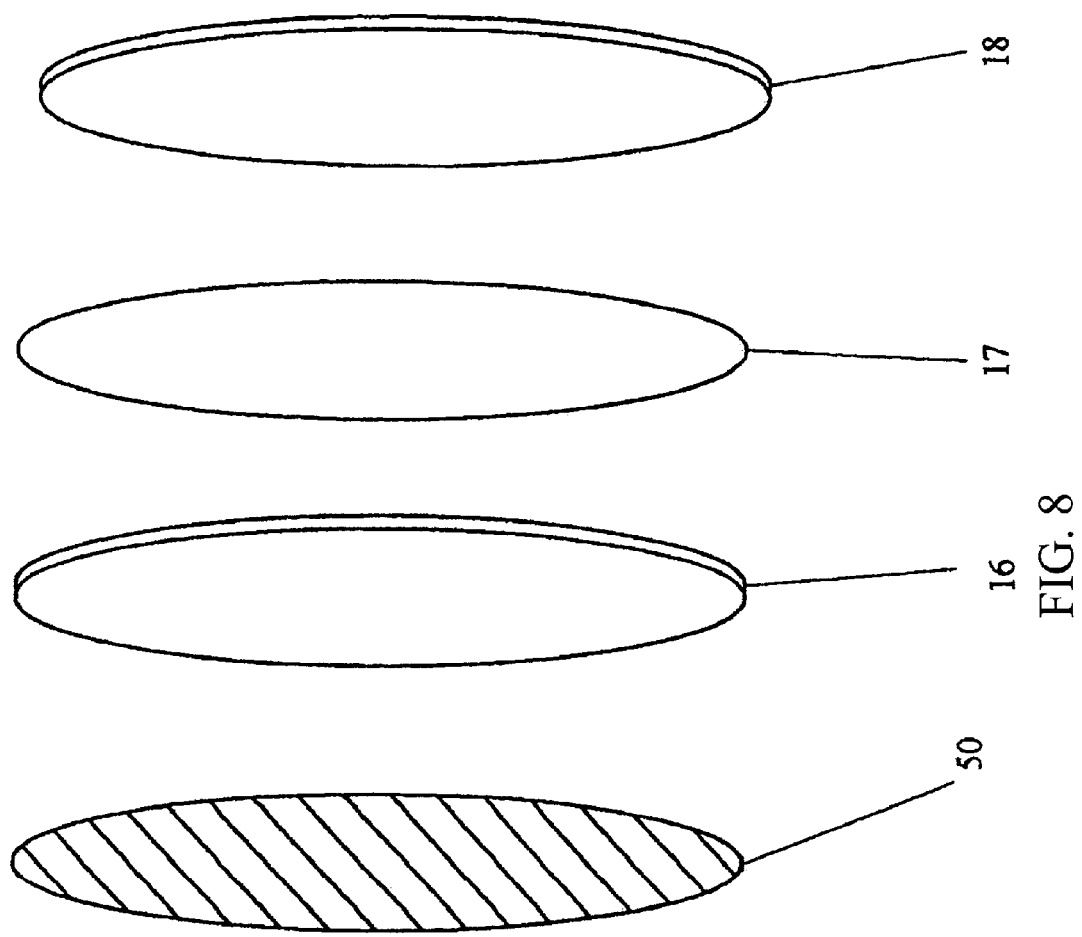

DUAL-FILTER OPHTHALMIC LENS TO REDUCE RISK OF MACULAR DEGENERATION

CROSS-REFERENCE TO RELATED APPLICATIONS

The present application is a continuation-in-part of U.S. application Ser. No. 11/303,433, filed Dec. 16, 2005, now U.S. Pat. No. 8,403,478 which is a continuation-in-part of U.S. application Ser. No. 10/856,688 filed May 28, 2004 (now U.S. Pat. No. 7,066,596), which is a continuation-in-part of U.S. application Ser. No. 10/000,062 filed Nov. 3, 2001 (now abandoned), which derived priority from U.S. Provisional Application No. 60/245,304 filed Nov. 3, 2000.

BACKGROUND OF THE INVENTION

1. Field of the Invention

The present invention relates to optical lenses for glasses, contact lenses and intraocular lenses (IOLs), more particularly, to an improved ophthalmic lens (for prescription and non-prescription glasses, sunglasses, contact lenses and intraocular lenses or "IOLs") incorporating dual filters that combine to provide protection against macular degeneration by reducing harmful light transmission and ocular photochemical damage.

2. Description of the Background

The goal of most protective lenses (including those in high-end sunglasses) is to provide a particular light transmission profile that yields the highest protection and perfect vision under all light conditions. To accomplish this goal, lenses for protective eyewear and IOLs often include filters that achieve a particular transmission profile. There are different perspectives on the optimum transmission profile what the best transmission profile is.

The ocular hazards from ultraviolet solar radiation are well established. Ultraviolet radiation falls within a range of wavelengths below visible light, generally between 100 and 400 nanometers. Long UVA radiation occurs at wavelengths between 315 and 400 nanometers. UVB radiation occurs between 280 and 315 nanometers. UVC radiation occurs between 200 and 280 nanometers. Wavelengths between 100 and 200 nanometers are known as vacuum UV. Vacuum UV and UVC are the most harmful to humans, but the earth's ozone layer tends to block these types of ultraviolet radiation. According to Prevent Blindness America, the American Academy of Opthalmology, and the American Optometric Association, the hazards from ultraviolet exposure include eyelid cancer, cataract, pterygium, keratitis, and macular degeneration. Cataracts are a major cause of visual impairment and blindness worldwide. "We've found there is no safe dose of UV-B exposure when it comes to the risk of cataracts, which means people of all ages, races and both sexes, should protect their eyes from sunlight year-round." Infeld, Karen, *Sunlight Poses Universal Cataract Risk*, Johns Hopkins Study http://www.eurekalert.org/releases/jhu-sunposcat.html (1998). Indeed, age-related macular degeneration (AMD) is the leading cause of blind registration in the western world, and its prevalence is likely to rise as a consequence of increasing longevity. Beatty et al., *The Role of Oxidative Stress in the Pathogenesis of Age-Related Macular Degeneration, Survey of Opthalmology*, volume 45, no. 2 (September-October 2000).

More recently, the Age-Related Eye Disease Study (AREDS) was published. This was a major clinical trial sponsored by the National Eye Institute, one of the Federal government's National Institutes of Health. The AREDS investigated the history and risk factors of age-related AMD, as well as how to reduce the risk of advanced age-related AMD and its associated vision loss. It was found that high levels of antioxidants and zinc significantly reduce the risk of advanced age-related AMD (reported in the October 2001 issue of Archives of Opthalmology).

What is less well-known is that visible blue light can contribute to age-related AMD and its associated vision loss, causing significant damage over time. The optical spectrum (light or visible spectrum) is the portion of the electromagnetic spectrum that is visible to the human eye. A typical human eye will respond to wavelengths from 400 to 700 nm. This visible blue light falling within the 400-475 nm range can also cause damage over time. A ten-year Beaver Dam Eye Study was completed and reviewed in the Arch Opthalmology, vol. 122, p. 754-757 (May 2004). This study proves a direct correlation between the incidence of blue light and AMD but does not attribute the correlation to any particular blue light wavelengths. A number of other references suggest a correlation between the visible blue light contribution of sunlight and AMD. See, for example, West S. K. et al., Arch. Ophthaomol., 1989; 107: 875; Cruickshanks K J et al., Arch. Ophthaomol., 1993; 111: 514; Young R. W., Survey Ophthaomol., 1988; 32: 252; Mitchell P. Et al., Survey Ophthaomol., 1997; 104: 770.

The present inventor contends that there is a significant need for protective lenses that selectively block visible blue light in the 415-475 nm range. As the entire population is potentially exposed to sunlight, the odds ratio of 13.6 and 2.19 for high exposure to visible blue light and AMD represent quite robust evidence in support of the sunlight/AMD hypothesis. Consequently, a lens that dramatically reduces visible blue light (preferably in combination with a high degree of UVA and UVB protection, and without sacrificing visual acuity) will preserve visual function, and would be advantageous to the user This transmission profile is difficult to achieve with conventional lens technology. The Food and Drug Administration recommends that sunglasses, prescription or non-prescription, block 99% of UVB and 95% of UVA, and most sunglasses on the market meet these criteria. The American National Standards Institute (ANSI) rates nonprescription eyewear for their potential to protect the human eye against solar radiation. However, many feel that the ANSI Z80.3 standard falls short. For example, the Z80.3 standard does not require specific quantification of the precise transmittance of ultraviolet radiation, nor blue light or infrared radiation, or reflected or scattered solar radiation that is not transmitted through the lens but still reaches the human eye. Some sunglasses for outdoor enthusiasts can achieve 99% of both UVA & B reduction, but afford no protection against visible blue light. This is because the existing lens technologies only afford control over glare, as well as the UVA & UVB transmission profile of lenses. These technologies include polarizers, color filters and mirror coatings.

Polarizers eliminate the horizontal transmission of reflected light through the lens to the eyes of the wearer. The polarizing layer blocks light at certain angles, while allowing light to transmit through select angles. This helps to negate annoying glare reflected off other surfaces such as water, snow, automobile windshields, etc. A polarized filter is produced by stretching a thin sheet of polyvinyl alcohol to align the molecular components in parallel rows. The material is passed through an iodine solution, and the iodine molecules likewise align themselves along the rows of polyvinyl alcohol. The sheet of polyvinyl is then applied to the lens with colored rows of iodine oriented vertically in order to eliminate horizontally reflected light. The sheet of polyvinyl may be applied to a lens in one of two ways: the lamination method or the cast-in mold method. To polarize a glass lens, the lamination method is used whereby the polyvinyl filter is sandwiched between two layers of glass. For plastic lenses, the cast-in mold method is used whereby the polyvinyl filter is placed within the lens mold. Relevant prior art patents might be seen in the Schwartz U.S. Pat. No. 3,838,913 and Archambault U.S. Pat. No. 2,813,459. A significant benefit of polarized lenses is the elimination of glare from reflective surfaces such as water.

Color filters can also provide excellent ultraviolet obstruction properties. For example, U.S. Pat. No. 4,878,748 to Johansen et al. (SunTiger) issued Nov. 7, 1989 discloses an optical lens with an amber filter having selective transmissivity functions. This is the original "Blu-blocker" patent for amber lenses that includes a sharp cut-on filter that blocks harmful Ultraviolet radiation and blue light. A combination dye is used to substantially block all wavelengths between 300 and 549 nanometers. The lens is substantially transparent to wavelengths greater than 636 nm which are most useful for high visual acuity in a bright sunlit environment. Similarly, U.S. Pat. No. 5,400,175 (SunTiger) discloses an amber filter having a cut-on at 550 nm. However, color-differentiation is highly distorted due to the deep orange tint as their deep yellow-orange tint weakens color differentiation. Indeed, many tinted sunglasses do not provide the capability to recognize traffic lights or other necessary color cues.

Various mirror coatings have been available to the sunglass industry for decades. These mirror coatings can be applied to the front and/or back surface of a lens to further reduce glare and provide protection against infrared rays. Metallic mirrors comprise a layer of metal deposited directly on a glass lens to create the equivalent of a one-way mirror. See, e.g., U.S. Pat. No. 4,070,097 to Gelber, Robert M (1978). However, like polarizers, metallic oxide coatings are not color-selective and cannot selectively block visible blue light in the 400-475 nm range.

Rugate filters are a less well-known lens technology in the context of protective eyewear. A Rugate filter is an interference coating in which the refractive index varies continuously in the direction perpendicular to the film plane. The addition of a rugate filter to a lens can potentially block visible blue and UV light, while allowing other visible light to pass unimpeded. Rugate filters are wavelength specific filters that have existed for about a decade. Their simple periodic continuous structures offer a much wider set of spectral responses than discrete structures, and they typically exhibit a spectrum with high reflectivity bands. This allows the possibility of making high reflectivity mirrors with very narrow bandwidth. Moreover, they can be formed so as not to distort bandwidths outside the stop-bands. In contrast to tinted lenses, this provides the capability to recognize traffic lights and other necessary color cues. An overview of Rugate filter technology can be found at Johnson et al., "Introduction to Rugate Filter Technology" SPIE Vol. 2046, p. 88-108 (November 1993), inclusive of how a simple rugate filter is derived from Fourier analysis. Other examples can be found in U.S. Pat. No. 5,258,872 "Optical Filter" by W. E. Johnson, et al. and disclosed in U.S. Pat. No. 5,475,531 "Broadband Rugate Filter" by T. D. Rahminow, et al.

Despite the foregoing options, there currently are no protective lenses that can block visible blue light in the 415-475 nm range without otherwise degrading the visible light transmission spectra. The foregoing is possible by combining two filters to establish a selective light transmission profile under all light conditions that maximizes the degree of protection as well as clarity of vision. The present dual-filter ophthalmic lens technology can be incorporated in ophthalmic lenses, sunglasses, polarized sunglasses, intraocular lenses and contact lenses.

SUMMARY OF THE INVENTION

It is an object of the present invention to provide a dual filter technology incorporated in an optical lens that maximizes the degree of protection as well as clarity of vision under all light conditions.

It is another object to provide a dual filter technology in an optical lens that is well-suited for ophthalmic lenses, sunglasses, polarized sunglasses, intraocular lenses and contact lenses.

According to the present invention, the above-described and other objects are accomplished by providing an improved dual-filter lens for protective eyewear that combines a first filter for blocking essentially 100% of UV light, and second filter for filtering blue light. The first filter may comprise a multi-layered dielectric mirror layer 14 or Rugate filter 50, and the second filter may comprise dye-impregnated lens layer(s) 16, 18 or Rugate filter 50. Again, the first filter blocks essentially 100% of UV light, while the second filter establishes an increasing transmission profile that cuts on sharply at approximately 415 mn, and establishes an increasing transmission profile between approximately 415 nm to about 475 nm. The cut-on slope rises approximately 0.15% in transmissivity for every nanometer of increasing wavelength change, with a maximum filtering effect within the 440-465 nm range. These dual filters provide a balanced light transmission profile that reduces harmful light transmission and prevents macular degeneration, cataracts and other ocular injuries, while still preserving visual acuity.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 3 is a definition analysis showing the definition profile of the improved lens as in FIG. 2 (analysis by Colts Laboratories).

FIG. 8 shows a Rugate filter 50 which may be incorporated in place of the dye (as the second filter), or in place of the multi-layered dielectric mirror layer 14 (as the first filter) of FIG. 1.

DETAILED DESCRIPTION OF THE PREFERRED EMBODIMENTS

Disclosed is an improved lens designed for protective eyewear that includes a dual filter including a first filter for blocking essentially 100% of UV light, and a second filter for filtering blue light. The lens is well-suited for prescription or non-prescription eyewear, inclusive of ophthalmic lenses, sunglasses, polarized sunglasses, intraocular lenses and contact lenses and IOLs. The lens comprises a plastic, polycarbonate (CR-39), Trivex® or other polymeric lens incorporating a first filter for blocking essentially 100% of UV light, and a second filter to selectively block visible blue light, the combination additionally giving a high degree of UVA and UVB protection with a well-balanced light transmission profile under all light conditions, thereby maximizing protection while preserving clarity of vision.

Figure 1:
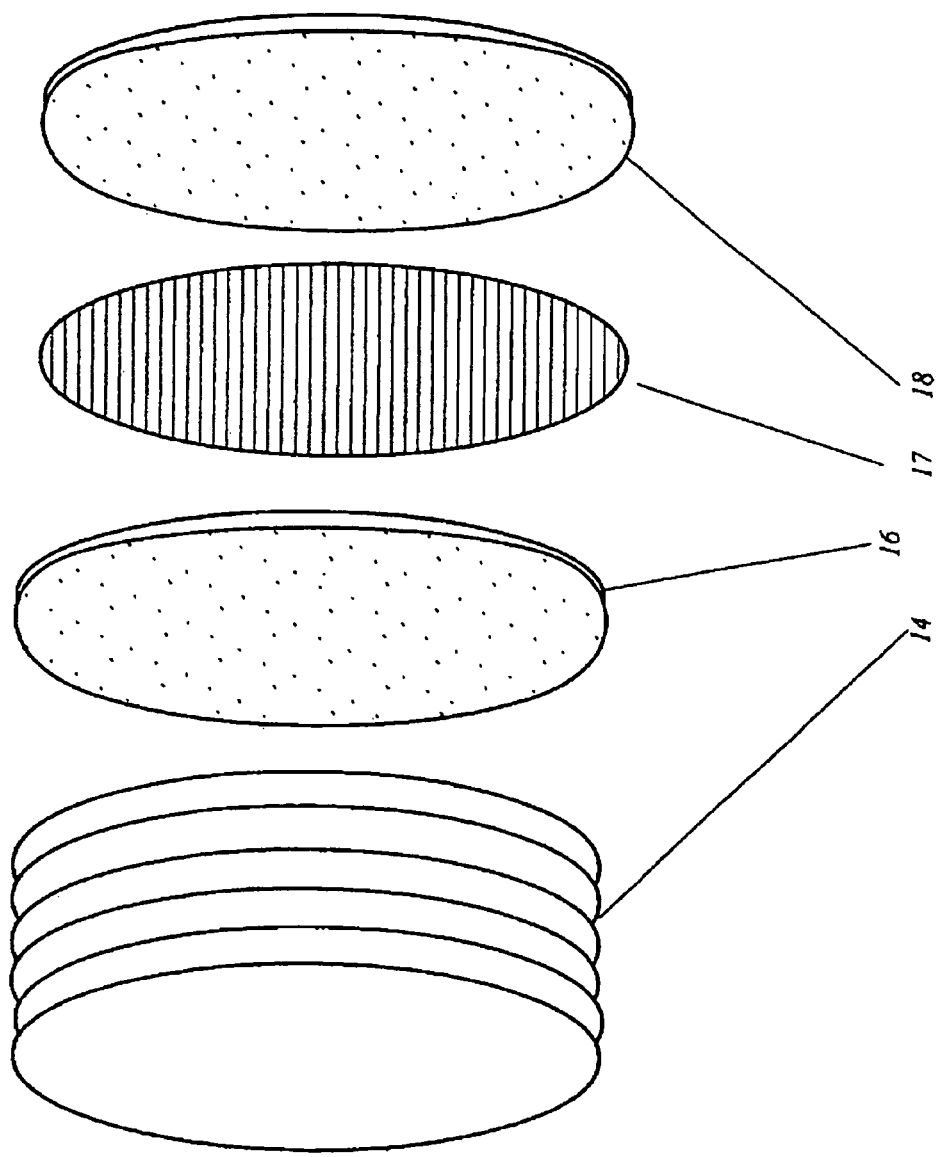
FIG. 1 is a perspective exploded sketch showing the possible lens layers according to the present invention.

FIG. 1 is a perspective exploded sketch showing the various lens layers mentioned above according to a multi-layer embodiment of the present invention. The multi-layer lens includes a dual filter comprising a first filter for blocking essentially 100% of UV light, and a second filter for filtering blue light. The first filter may comprise a multi-layered dielectric mirror layer 14. For example, U.S. Pat. No. 5,844,225 to Kimock et al discloses an optical coating design formed in a multi-layer "dielectric stack" configuration for producing an anti-reflection feature, plus a method for fabricating a coated substrate product. Kimock et al. '225 also suggests various stacked layers inclusive of titanium oxide, nitride, zirconium nitride, boron nitride, yttrium oxide, silicon oxide, silicon dioxide, zirconium oxide, silicon carbide, aluminum oxide, aluminum nitride, and various mixtures thereof that are transparent to light in the visible region of 350 to approximately 750 nanometers, but block the UV range. The first filter of the present invention may employ a similar method to create a particular stacked layer 14 which actually comprises six equal-thickness thin film layers (2-3 nm total) of titanium oxide, silicon dioxide (quartz), zirconium oxide, and chromium, each thin film layer being vacuum deposited separately in alternating 90 degree angles to provide a reflective mirror finish. Dielectric mirrors in general combine high reflection values with outstanding durability characteristics. These coatings can generally exhibit significantly higher reflectance values than metallic films over specific wavelength intervals. The present stacked dielectric mirror layer 14 with particular constituents applied in alternating angular deposits further optimizes the lens to reduce light transmission through the entire UV and visible light spectrum.

The second filter for filtering blue light may be one or more dyes incorporated in the plastic, polycarbonate (CR-39), Trivex® or polymeric lens 16 and/or 18. Either CR-39 (plastic) or polycarbonate lens blanks may be used as both types of materials are capable of molecular bonding. In the illustrated embodiment, high-contrast blue-blocking amber dye is molecularly bonded in the CR-39 (plastic) layers 16, 18 which in combination with the dielectric mirror 14 yield the excellent light transmission profile of the present invention. Specifically, the second filter selectively filters blue and violet light pursuant to a sharp "cut-on" filter that establishes an increasing transmission profile that cuts on at approximately 415 nm.

Optionally, a polarizing filter layer 17 may be bonded between the polymer layers 16, 18. For the polarizing filter layer 17, there are basically two types of polarized lens constructions, laminated and cast suspended filter. Laminated lenses are made by sandwiching the polarized film between layers of plastic or glass, utilizing an adhesive to hold it together. The adhesive can make the laminated lens appear hazy and the adhesion can fail when subjected to high heat and processing forces. The CR-39 polarized lens 16 of the present invention is cast with a suspended filter and does not rely upon adhesives to hold everything together. Molecular bonding is used to chemically join the lens layers 16 18, thus totally encapsulating the polarizing filter layer 17 between the two CR-39 plastic lens layers 16, 18, thereby avoiding haze and delamination.

Figure 2:
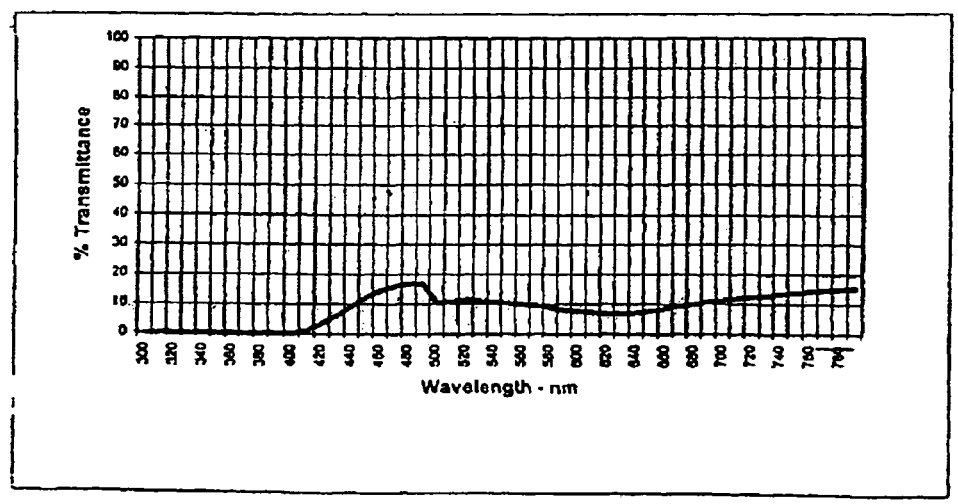
FIG. 2 is a spectral analysis showing the light transmission profile of the improved lens with dual filters according to the present invention (analysis by Colts Laboratories of Clearwater Fla., a leading and accredited analysis laboratory).
Figure 4:
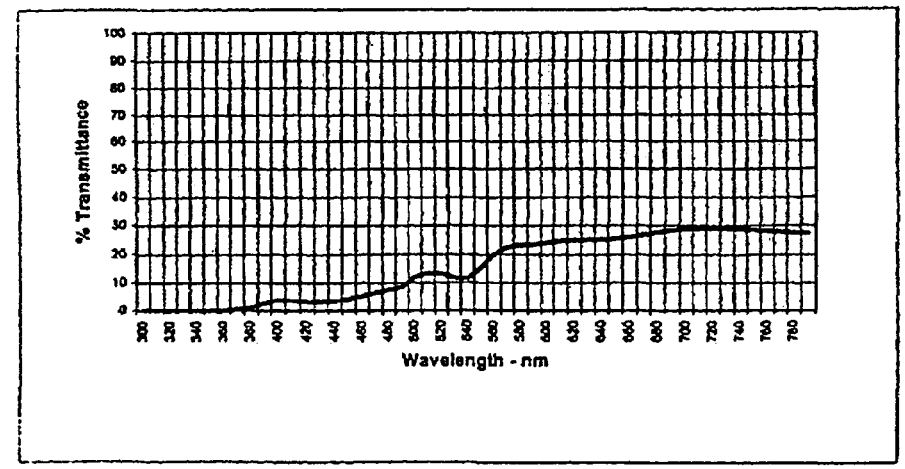
FIG. 4 is a spectral analysis for comparative purposes showing the light transmission profile of competing Ray Ban™ sunglass lens (Colts Labs).
Figure 5:
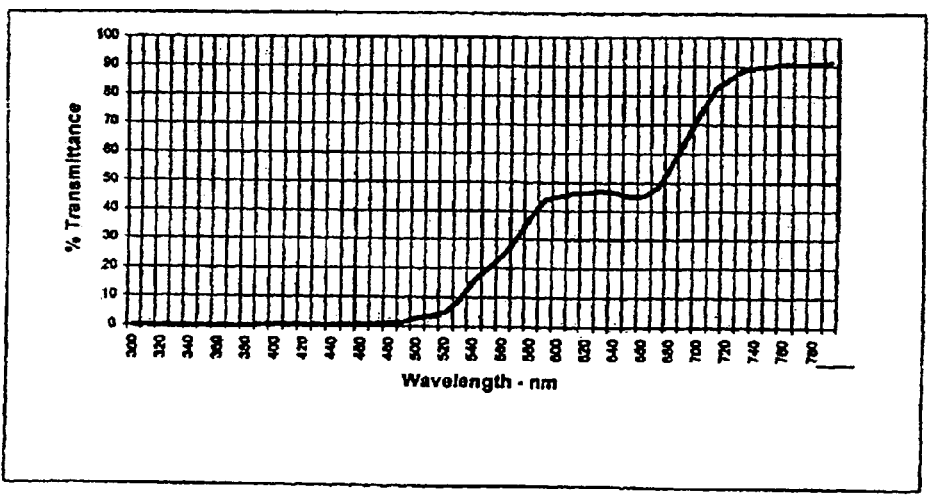
FIG. 5 is a spectral analysis for comparative purposes showing the light transmission profile of competing Blu-Blocker™ sunglass lens (Colts Labs).
Figure 6:
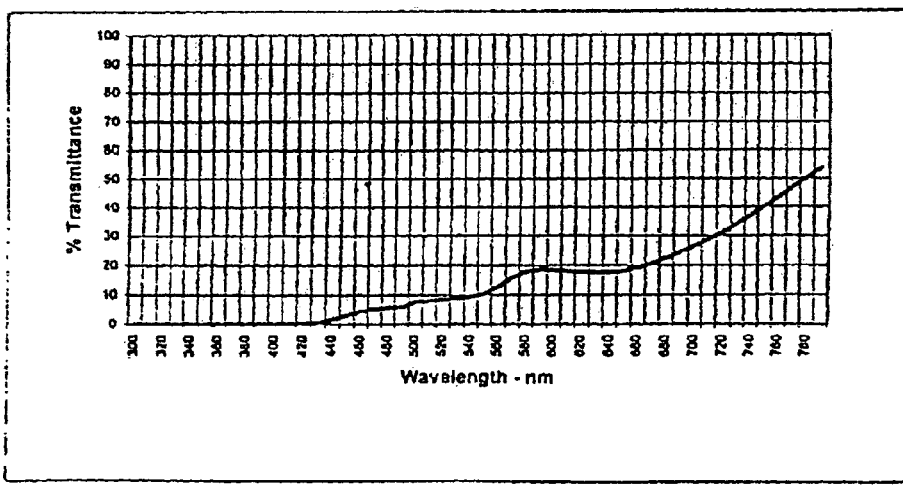
FIG. 6 is a spectral analysis for comparative purposes showing the light transmission profile of competing Costa Del Mar™ sunglass lens (Colts Labs).
Figure 7:
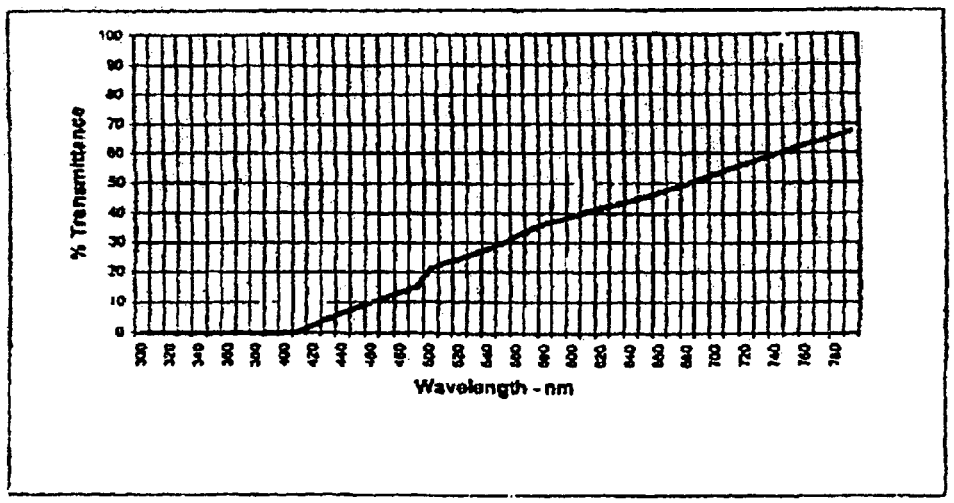
FIG. 7 is a spectral analysis for comparative purposes showing the light transmission profile of competing Melavision™ (Photoprotective Technologies) sunglass lens (Colts Labs).

FIG. 2 is a spectral analysis showing the light transmission profile of the improved lens with dual filters according to the present invention (analysis by Colts Laboratories of Clearwater Fla., a leading and accredited analysis laboratory). A cut-on filter is an optical filter that substantially blocks all wavelengths shorter than the cut-on wavelength and substantially transmits all wavelengths that are longer than the cut-on wavelength, and the cut-on slope represents the transition between the substantially blocking region and the substantially transmissive region. In the present case, it can be seen that the second filter establishes an increasing transmission profile that cuts on sharply at approximately 415 nm, and establishes an increasing transmission profile between approximately 415 nm to about 475 nm. The cut-on slope rises approximately 0.15% in tranmissivity for every nanometer of increasing wavelength change, with a maximum filtering effect within the 440-465 nm range.

FIG. 3 is a definition analysis showing the definition profile of the improved lens as in FIG. 2 (analysis by Colts Laboratories).

Alternatively, the second filter may comprise a Rugate filter to even further reduce the visible blue light, UV, and infrared and laser energy. While more expensive to produce, Rugate filters are effective bandpass filters that can be made to exhibit the same light transmission profile.

Referring to FIG. 8, a Rugate filter 50 is show to be incorporated as the second filter in place of the dye, or as the first filter in place of the multi-layered dielectric mirror layer 14 of FIG. 1. The Rugate coating 50 may be a combination of Silicon, Oxygen and Nitrogen compounds in specific ratios providing a pre-defined variation in the index of refraction. For example, Silicon Dioxide ($SiO_2$) provides an index of refraction of about 1.5 while Silicon Nitride ($Si_3N_4$) provides a value of about 2.0. For present purposes, the variation in the index of refraction is calculated in order to complement or supplement the above-described dielectric mirror, e.g., by further reducing the visible blue light as well as infrared and laser energy. It should be noted that other combinations can be used to achieve this desired light transmission profile. For example, tantala/silica and hafnia/silica combinations have been used for multilayer coatings. These materials are deposited by means of a plasma-enhanced chemical vapor deposition process (PECVD) varying the flow rate of Ammonia gas ($NH_3$) and Nitrous Oxide gas ($NO_2$) in the presence of a mixture of Silane gas ($SiH_4$) and Argon, though it should be understood that other combination of materials can be used. See, for example, Goetzelmann et al., "UV Coatings Produced with Plasma-ion-assisted Deposition", SPIE Vol. 3738, p. 48 57 (September 1999), which describes the plasma-ion-assisted deposition for the production of multilayer coatings for the visible and NIR spectral range including Rugate filters. The Rugate filter is deposited on one of the lens layers 16, 18 via plasma-enhanced chemical vapor deposition using a vacuum chamber in which, for example, lens layer 16 is placed with the Rugate filter coating 50 deposited thereon by a traditional evaporation method. The coating 50 is deposited on the lens layer 16 using an increment deposition approach, and this can be implemented by computer control to achieve the desired sinusoidal Rugate profile. Plasma-assist coating then relies on plasma to bombard the thin Rugate film deposited by the traditional evaporation method in order to improve the film's micro-structure. In this type, the main chamber of a vacuum system is maintained at a residual pressure around 10 mil by an inert, ionized sputter-gas (for example, argon) called a plasma. An RF generator generates the plasma within the chamber, and the flow of process gases are controlled by a computer in a known manner. Plasma sputtering generally needs a certain concentration of gas molecules, typically 1 to 10 millitorr of residual pressure, to operate. This results in a single layer Rugate film 50 having a continuously varying index of refraction along a thickness direction with a number of maxima and minima in the index. The variation in the index of refraction may be calculated in a known manner to provide a Rugate filter 50 in place of or as a supplement to the foregoing dielectric mirror to further preserve visual integrity while also reducing glare, adding contrast, and maintaining color balance. Preferably, the Rugate filter used herein is color-neutral so as not to alter the light transmission profile of the other lens layers. See, for example, Johnson et al., "Color Neutral Rugate Filters", SPIE Vol. 2046, p. 132 140 (November 1993), which describes a transmissive rugate filter which is designed to reflect a portion of the visible spectrum and yet not appear to have a dominant color. (RC, remember there is no explanation of the item #13)

The combination of the above-described first filter for blocking essentially 100% of UV light, and second filter for filtering blue light dramatically reduces glare and increases contrast in varying types of light conditions. The first filter may comprise a multi-layered dielectric mirror layer 14 or Rugate filter 50, and the second filter may comprise dye-impregnated lens layer(s) 16, 18 or Rugate filter 50. In either case the dual filters combine to provide protection against macular degeneration by reducing harmful light transmission and ocular photochemical damage.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

I claim:

1. A lens comprising:
   a polymer material; and
   at least two filters incorporated in the polymer material of said lens, said two filters combining to block all UV light and selectively filter blue and violet light pursuant to a sharp cut-on filter that blocks substantially all wavelengths shorter than 415 nm, cuts on at approximately 415 nm, and establishes a transmission profile consisting of a continuously increasing slope from 415 nm to at least 475 nm.

2. The lens according to claim 1, wherein one of said at least two filters is a first colored dye.

3. The lens according to claim 2, wherein another of said at least two filters is a Rugate filter.

4. The lens according to claim 2, wherein another of said at least two filters is a second colored dye.

5. The lens according to claim 2, wherein said lens material comprises plastic (CR-39).

6. The lens according to claim 5, wherein 99% of visible blue light is absorbed between 400-475 nm.

7. The lens according to claim 1, wherein said s is a sunglass lens.

8. The lens according to claim 1, wherein said lens is a contact lens.

9. The lens according to claim 1, wherein said lens is an intraocular lens.

10. The lens according to claim 2, wherein said first colored dye is one from among the group of high-contrast blue-blocking amber-tint and color discriminating grey tint.

11. The lens according to claim 3, wherein said Rugate filter comprises a bandstop rugate filter for selectively filtering visible blue light between approximately 415 nm to about 475 nm to preserve macular integrity.

12. The lens according to claim 1, whereby one of said two filters is a band pass filter.

13. The lens according to claim 1, whereby one of said two filters blocks UV light.

14. The lens according to claim 1, whereby one of said two filters, filters blue light.

15. The lens according to claim 1, wherein said transmission profile consists of a continuously increasing slope that rises in transmissivity by approximately 0.15% for every nanometer of increasing wavelength to about 475 nm.

16. The lens according to claim 1, wherein said lens is an eyeglass lens.

* * * * *